United States Patent [19]

Cox et al.

[11] Patent Number: 5,493,994
[45] Date of Patent: Feb. 27, 1996

[54] NON-INVASIVE FORCED OXYGEN ENRICHMENT OF FERTILIZED AVIAN EGGS

[76] Inventors: James P. Cox; Robert W. Duffy Cox, both of 246 E. Bartlett Rd., Lynden, Wash. 98264

[21] Appl. No.: 253,750

[22] Filed: Jun. 3, 1994

Related U.S. Application Data

[63] Continuation-in-part of Ser. No. 746,940, Aug. 19, 1991, Pat. No. 5,431,939, which is a continuation-in-part of Ser. No. 674,495, Mar. 25, 1991, Pat. No. 5,283,072, which is a continuation of Ser. No. 349,974, May 8, 1989, abandoned, which is a continuation of Ser. No. 196,878, May 19, 1988, abandoned, which is a continuation of Ser. No. 70,597, Jul. 8, 1987, abandoned, which is a continuation of Ser. No. 748,086, Jun. 24, 1985, abandoned.

[51] Int. Cl.$^6$ .......................... A01K 45/00; A01K 29/00; A23J 3/00; C12N 5/00
[52] U.S. Cl. .............. 119/6.8; 119/174; 426/47; 435/240.2; 800/2
[58] Field of Search ............. 800/2; 435/240.2; 426/47; 119/6.8, 174

[56] References Cited

U.S. PATENT DOCUMENTS

| 2,236,773 | 4/1941 | Fischer. |
| 2,776,214 | 1/1957 | Lloyd et al.. |
| 3,028,245 | 4/1962 | Mink et al.. |
| 3,144,342 | 8/1964 | Collier et al.. |
| 3,364,037 | 1/1968 | Mink. |
| 3,658,558 | 4/1972 | Rogers et al.. |
| 4,524,082 | 5/1985 | Loit. |
| 4,524,083 | 6/1985 | Loit. |
| 4,957,759 | 9/1990 | Swartzel et al.. |

OTHER PUBLICATIONS

H. Rahn, C. Paganelli, A. Ar; Date and title unknown.
H. Rahn, C. Paganelli, A. Ar; "How Bird Eggs Breath", Feb. 1979 Scientific American.
N. Kurti, H. This–Benckhard; "Chemistry and Physics in the Kitchen", Apr. 1994 Scientific American.
Christensen et al (1988) Poultry Science 67, 956–960.
Hesselman et al (1981) Poultry Science 60, 2664–2671.
Wilson et al (1978) Poultry Science 57, 403–407.
Krueger, Kenneth K.; date unknown; "Fertility in Female Turkeys: How to Manage It?".
Krueger, Kenneth K.; date unknown; "A Proposal to Initiate Intensive Research on Improving Hatchability in Turkeys".

Primary Examiner—Jacqueline M. Stone
Assistant Examiner—Deborah Crouch
Attorney, Agent, or Firm—Graybeal Jackson Haley & Johnson

[57] ABSTRACT

A method and products are disclosed in which a fertilized egg is non-invasively infused with oxygen such that the structural integrity of the shell of the egg is not compromised. The method comprises the step of subjecting the external surface of the eggshell to the oxygen under a condition of at least one of vacuum and positive pressure. The oxygen is from a substance selected from the group consisting of oxygen, nascent oxygen, liquid oxygen, oxone, ozone, hydrogen peroxide, and potassium permanganate.

12 Claims, 6 Drawing Sheets

NON-INVASIVE FORCED OXYGEN ENRICHMENT OF FERTILIZED AVIAN EGGS

CROSS-REFERENCE TO RELATED APPLICATIONS

This application is a continuation-in-part of U.S. application No. 07/746,940 filed Aug. 19, 1991, U.S. Pat. No. 5,431,939. The parent application is a continuation-in-part of U.S. application No. 07/674,495 filed Mar. 25, 1991, U.S. Pat. No. 5,283,072 which was a continuation of U.S. application No. 07/349,974 filed May 8, 1989 and abandoned, which was a continuation of U.S. application No. 07/196,878 filed May 19, 1988 and abandoned, which was a continuation of U.S. application No. 07/070,597 filed Jul. 8, 1987 and abandoned, which was a continuation of U.S. application No. 06/748,086 filed Jun. 24, 1985 and abandoned.

BACKGROUND OF THE INVENTION

In non-extinct species, the avian egg is known to range in mass from 0.25 to 1,500 grams. The common poultry egg has an average weight of about 60 grams. The common fertilized poultry egg is both self-contained life support system and cradle. However, the life support system is flawed. It lacks oxygen. All other elements are present, including the fuel with which the fire of life will be sustained through the twenty-one day journey.

Oxygen is the driving force which feeds the biological matrix from which the new Life is fashioned. The cycle of synthesis begins at the moment "set" occurs, i.e. the moment that the process of viability is initiated when the temperature of the fertilized egg exceeds about 68° F. to about 70° F. for any substantial period of time..

From the first moment the process of viability begins, the margins of success are tenuous. A race between catabolic and anabolic processes is initiated as life force courses forward. Oxygen must be obtained and the apparatus for gathering it must be fashioned within the margins of the small reserves available. Never again will the challenge be quite so great or the margins so small. The slightest unfavorable environmental conditions, and the battle is lost.

Unfortunately, the optimal conditions for incubation also favor internal competitive breakdown forces and external invasive ones. Ideal conditions in the incubator, darkness, moderately high humidity and temperatures of 99.5° F.±0.5° F. are nearly optimal for microbial life which will proliferate around and inside the egg shell. Thus, a multitude of foreign life forms are present. Some may be innocuous, others competitors or antagonists, and it is even possible that some familiar types such as Salmonella are symbiotic to the avian neonate.

The viability processes begin at the center but are subsequently focused outward to the extremities of the egg. Surrounding the embryo is a laminar set of membranes. The outermost layer (actually,, a bi-layer) lies against the shell. The innermost layer is referred to as the chorioallantoic membrane and envelopes the albumen and yolk.

The outer shell is made up of crystalline calcium and is many times thicker than the inner shell and other adjacent membranes combined. The external surface has trumpet-shaped pores which run through the shell to the surface to the membrane. Typically, there are about 7,000 to 17,000 pores distributed over the shell surface, the highest density being at the rounded end (top) of the egg proximal to the air sac located adjacent to the interior of the shell. The air sac is a space created by a parting between the outer and inner shell membranes wherein the outer membrane remains attached and the inner (chorioallantoic) membrane is detached from the outer shell membrane. The separation between the two membranes creates the air sac which serves as a gas exchange depot, sometimes referred to as the "dumb" lung. The dumb lung respires in response to changes in temperature and atmospheric pressures. The dumb lung also grows larger and larger as the ovum takes up less and less space in using up its reserves, the byproducts of which pass through the lung to the outside. Once incubation has started, the embryo provides a network of arteries and veins to the working side of the lung, which thereafter allows for efficient gas exchange through the lung.

Prior art teaches that as pressure is applied and then increased to fertilized eggs, fatalities from the onset of pressure very quickly increase to 100%. Prior art also teaches that as vacuum is applied and then increased to fertilized eggs, fatalities from the onset of pressure very quickly increase to 100%. Furthermore, prior art shows that when ambient oxygen is increased or decreased above normal concentrations (21%) during incubation, the hatch rate of fertilized eggs decreases markedly. In sum, prior art shows that there is no known advantage to any process applied to fertilized eggs prior to incubation, and that fertilized eggs are adversely affected by such treatments.

Handling and artificial incubation methods have developed over the last century to create the best known conditions of humidity, air circulation, stable storage and incubation temperatures, and motion to provide maximum hatch of fertilized egg stock. For storage of fertilized egg stock, air sac (top) up for no longer than twenty clays at a temperature of about 55° F. is preferred. For incubation, air sac (top) up, humidity of about 60% during the first 18 days and about of 70% the last three days, a temperature of 99.5° F.±0.5° F. with a gentle, cradle-like rocking motion, timed about once every ninety minutes, and filtered, recirculated ambient air (21% $O_2$) is preferred. These conditions result in more or less maximum average hatches. Percentages of average hatches vary considerably depending upon the storage age of fertilized egg stock and the age, type and conditions of laying flocks from which they are derived. In general, the range is from about 80% to under 86% hatch, or a 14% to 20% mortality less the percentage of unfertilized eggs.

Shortly after hatching, chicks are injected with vaccines (such as Marek's) to prevent flock diseases. Significant expense and mortality are incurred due to the invasive nature of the injection.

Improvements in the overall healthiness of the hatched chicks strongly influences efficiencies with respect to grow-out factors of the flock, i.e. percentages of grow-out mortality, size, strength, fertility, feed conversion, susceptibility to disease and, ultimately, overall commercial success of the flock as layers, breeders or broilers and fryers for meat. Improvements related to better disease resistance, feed conversion, strength and increased commercial success from grow-out are also desirable. Finally, the ability to provide early nutritional advantages, to provide medications related to improved mortality or growth, to alter or manipulate sex characteristics, to provide microbial synergists (probiotics), to control disease agents, including those of poultry and those pathogenic to humans, is also desirable.

SUMMARY OF THE INVENTION

Oxygen as defined herein includes O (oxone), $O_2$, $O_3$ (ozone) or any convenient source thereof including liquid oxygen, hydrogen peroxide and potassium permanganate, all of said chemicals above defined as oxygen-bearing chemicals.

Fertilized egg as defined herein includes both fertilized and pre-fertilized eggs (ovum)—also referred to as "vital eggs"—of any bird egg including chicken, turkey, goose, duck, raptor and parrot.

The present invention encompasses treating fertilized eggs prior to and in prenatal incubation phases by methods employing one or more of combinations of pressures, vacuums and above ambient levels of oxygen in the form of $O_2$ and/or $O_3$, or sources thereof, to non-invasively transfer the $O_2$ and/or $O_3$ through the egg shell without compromising the structural integrity of the shell.

When used according to the present invention to achieve the purposes as outlined, ozone exhibits vitalizing, as opposed to expected lethal properties, endowing the ovum with remarkably improved strength. This not only results in significantly higher survivability through incubation, but also greater strength through adulthood.

Contrary to the prior art, it is in the period of incubation and before the egg has developed oxygen-collecting organs or respiration that forced oxygen/ozone treatment demonstrates the most profound overall results. Increased hatch of fertilized eggs may be obtained by oxygen enrichment, preferably forced, and most preferably when the treatment is applied prior to or soon after incubation starts, with the oxygen being supplied into the egg spaces and interstices—even in high concentration levels which would normally be considered lethal concentrations. Non-invasive oxygen augmentation may be accomplished in a variety of ways, including subjecting fertilized eggs to brief periods of vacuums and/or pressures in the presence of oxygen or oxygen-containing substances or carriers.

Non-invasive but forced perfusion of disease control vaccines of fertilized eggs, with or without simultaneous forced enrichment of oxygen, can also provide profound benefits in terms of reduced mortality and cost savings of inoculation. More certain inoculation and substantial reductions in hatchling injection mortality occur.

Additionally, non-invasive forced perfusion of growth, health and gender characteristics additives, such as aromatase, may be added with or without enriched oxygen, affording valuable benefits to treated hatched flocks including important "out of the shell" disease and infection control, improved growth, feed conversions and added overall robustness and vitality.

Moreover, the levels of enrichment required to improve survivability of fertilized eggs also endow the chicks with greater robustness, as shown by better feed conversions over the grow-out period. The result is much higher efficiencies of production. Feed conversion is a composite result which may be comprised of one or more other operative factors such as healthier, stronger, less diseased or more disease resistant chicks.

Also, the microbicidal effects of oxygen against poultry endemic bacteria, such as Salmonella, are realized; particularly if more active forms such as nascent and ozone oxygen are increased in the oxygen enrichment treatment. Finally, the present invention provides improved food safety, for it is axiomatic that healthier animals provide healthier, safer food products.

BRIEF DESCRIPTION OF THE DRAWINGS

The foregoing objects and attendant advantages of this invention will become more readily appreciated as the same becomes better understood by reference to the following detailed description when taken in conjunction with the accompanying drawings.

DETAILED DESCRIPTION OF THE PREFERRED EMBODIMENTS

I. OVERVIEW

A. Oxygen.

Application of oxygen may be calculated as any equivalent mole weight above atmospheric concentrations (20.946%) supplied to the fertilized egg. Oxygen includes allotropic forms, nascent oxygen, liquid oxygen and oxygen-containing compositions such as hydrogen peroxide ($H_2O_2$), potassium permanganate ($KMnO_4$), and the like. Mole weights, calculated as percentages of the oxygen in enrichment fluid supplied to the fertilized egg, may be calculated as $O_1$ (oxone) at mole weight 7.9997, $O_2$ (oxygen) at mole weight 15.9994, and $O_3$ (ozone) at mole weight 47.9982.

For purposes of increased hatchability of fertilized eggs, the working range of enrichment oxygen calculated as $O_2$, $O_3$ or a combination thereof which may be employed is from greater than ambient, and is from about 21% to about 99.9998%. The preferred range of oxygen is from about 25% to about 99.99%. The most preferred percentage of oxygen is 45%±4%. When reduction of indigenous microbes is the object, or an added object, the preferred range is from about 50% to about 95%, and the most preferred oxygen concentration is about 70%±5%.

For hatchability, the oxygen may be high purity oxygen or a mixture of high purity oxygen ($O_2$) and ozone ($O_3$) as liquids or gases. Oxygen sources may also be selected as hydrogen peroxide, potassium permanganate solution and other fluidized oxygen carriers. A mixture of $O_2$ and $O_3$ are preferred, from about 1 to about 250 parts per million of $O_3$ to $O_2$.

For hatchability and microbial control, a mixture of $O_2$ and $O_3$ may also be used, with $O_3$ in the range of about 10 to about 5,000 parts per million of $O_2$. A ratio of about 100 parts per million $O_3$ to $O_2$ is preferred. Though not preferred, $H_2O_2$, $O_2$ and $O_3$ may also be used in combination, or $H_2O_2$ may be used as an adjunct or treating agent in ranges of from about 0.001% to about 30% in aqueous solution. About 7%±about 4% is preferred. Aqueous solutions of potassium permanganate may range from about 0.001% to about 20% in aqueous solution, but are preferred in lower concentrations, i.e., about 3%±about 2%.

Oxygen working range by weight compared to weight of egg is about 0.0001 grams to about 20 grams per 1,000 grams of egg mass. As stated, the oxygen may be from any source, such as liquid oxygen, purified oxygen, oxygen or ozone dissolved or associated with water or other carrier(s) or solute(s), including but not limited to ambient air as an ozone carrier. The preferred range is from about 0.001 to about 9 grams per 1,000 grams of egg mass. The preferred amount is about 3.0 grams per 1,000 grams of egg mass. Where oxygen or an oxygen source alone is used as the treating agent or in a carrier (usually but not always one or both of air or water), the concentrations may range from more than ambient (21%) to about 99.9998%. The preferred range is from about 60% to about 99%. Some other preferred levels of oxygen as treating agent or ingredient thereof are: when applied as a gas including available oxygen in carrier, about 95%; when applied as a liquid with carrier(s), about 50%; when applied as a super-cooled or liquid gas, about 99.8%; when applied as a super-cooled liquid or gas containing at least 1 part per million ozone, about 99%; when applied as hydrogen peroxide solution, about 60%; and as hydrogen peroxide and/or permanganate solution containing at least 1 part per million ozone, about 70%. Ozonated mixtures of oxygen are the most preferred enrichment media..

B. Negative Pressure:

Fertilized eggs may be subjected to negative pressure at the external surface of the egg. One method is to place the egg in an enclosed plenum upon which is exerted negative pressure to create a vacuum. Vacuums are applied externally to the egg in order to create room within the egg for the oxygen, and to force enriched forms of oxygen(s) and/or oxygen-carrying substance(s) through the shell upon relief of negative pressure. Enrichment capacity of the egg is enhanced by disinfusing the vacuum of ambient gases previously present in internal spaces and as dissolved gases in the egg matter. This step is followed by judicious introduction of the selected oxygen enrichment mixtures into the vacuumized plenum and consequently into the egg, which is also in a state of negative pressure. Alternative methods of treatment may also be used, though the underlying principles remain operative.

The above method of treatment permits optimization of the maximum concentration of selected enrichment gases into the egg. Such means can be accomplished by pathways other than using a chamber or vessel. For example, the egg may be warmed to cause internal expansion, resulting in expelling of ambient internal gases, and then cooled in the presence of selected enrichment gases, whereupon the egg will take in enrichment gases and replace at least some of the original ambient gases present. Also, liquid oxygen, preferably containing ozone, may be applied by fine spray to the pores of the egg surface to infuse oxygen. Another example is to employ a pressure cup, such as a suction cup, which can be affixed by contact to the external shell surface, preferably immediately over the air sac where portion is at maximum density. By applying negative pressure vacuum through an aperture in the suction cup, the air sac and other portions of the egg are emptied of indigenous gases. Oxygen and other treating agents may then be infused through the shell pores by negative pressure and/ozc in a positive pressure stream. While not essential to minimal oxygen enrichment, treatment vacuums are preferred when gasses alone are employed. An exception to the use of vacuum is where the available oxygen or other treating agent is in a liquid or associated with a carrier, such as liquid oxygen, hydrogen peroxide solutions or potassium permanganate in aqueous solution, as examples. In these instances, a positively pressurized fluid stream containing perfusate alone may be directed across and forced through the pores adequately. However, as a rule both negative and then positive pressure are preferred steps.

The working ranges of vacuums which may be employed are from greater than ambient to about 29.99 inches of mercury for a short time period. The time range for application of preferred vacuums from ambient to about 29.50 inches of mercury is from about one second to twenty minutes. The preferred vacuum range is from about 2.00 inches of mercury to about 29.99 inches of mercury. The preferred time range for application of the above preferred range of vacuum is from about one to about ten minutes. The preferred vacuum, if no added pressure cycle is employed, is about 28.00 inches of mercury±1.5 inches of mercury. The preferred time at preferred vacuum, if no added pressure cycle treatment is employed, is about one and one half minutes±one minute. If a positive pressure cycle also is to be applied to the egg, then the preferred vacuum is still about 28.00 inches of mercury±1.75 inches of mercury for about one and one half minutes±one minute.

Generally, the time to achieve the elected vacuum may range from about one second to twenty minutes. Preferred times to achieve elected vacuums for all preferred ranges is from about thirty seconds to about ten minutes. Preferred time to achieve vacuum is about three minutes±1.5 minutes. If a given vacuum is achieved too quickly, such as 29.90 inches of mercury in one second, physical damage can occur to some eggs. The opposite is true for the time over which the vacuum is held. If held too long at higher vacuum ranges, e.g. above about 27 inches of mercury for twelve to thirty minutes, the unabated vacuum may cause damage to some eggs.

Negative pressure may not be required for lower efficiency treatment; positive pressure alone may be adequate. Of course, the reverse is also true. Where lower efficiency treatment is acceptable, however, positive pressure is usually preferred since it alone fills the air sac. All but the most modest (approximately three inches of mercury to sixteen inches of mercury) negative pressure treatment will collapse the air sac and the air sac can only be refilled by at least a small (approximately five to ten pounds per square inch in a plenum) positive pressure step.

C. Positive Pressure.

Positive as well as negative pressure without oxygen kills fertilized eggs. If positive and/or negative pressure is applied for a sufficient time period or at high or low enough pressure, even added oxygens will not prevent egg fatalities. The working range of positive pressures which may be employed are from slightly greater than ambient (about 3 pounds per square inch) to about sixty pounds per square inch for from about one second to about thirty minutes. The preferred range of pressure is from about two pounds per square inch to about thirty-five pounds per square inch for from about one second to about ten minutes. The preferred pressure and time is about fourteen pounds per square inch±three pounds per square inch for about one and one half minutes±one minute. The preferred pressure ranges when a vacuum is also employed are from about three pounds per square inch to about twenty pounds per square inch for from about four minutes to about fifteen minutes, but ranges of from about two pounds per square inch to about thirty-five pounds per square inch from about one second to about ten minutes are acceptable. Preferred pressure with vacuum is about fourteen pounds per square inch for about two minutes. Working ranges for pressure when applied to an oxygen-bearing fluid stream are from about twenty five pounds per square inch to about 150 pounds per square inch, and when applied to fluid stream bursts from about 100 pounds per square inch to about 1,500 pound per square inch.

II. SPECIFIC EXAMPLES

EXAMPLE 1

Figure 1:
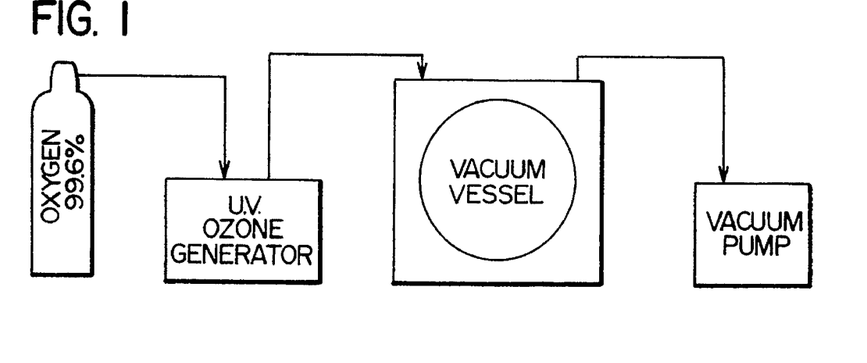
FIG. 1 is a block diagram of a first exemplary process of the present invention.
Figure 8:
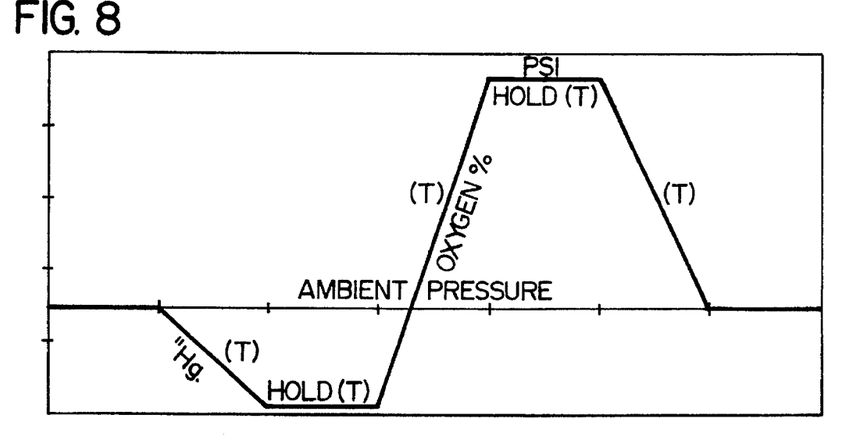
FIG. 8 is a graphical representation of the vacuum and pressure processes of the present invention.

Referring to FIGS. 1 and 8, fertilized eggs were force-enriched with oxygen as follows. Five hundred twenty eggs were treated and five hundred twenty were kept as controls. The average weight of the eggs was 60 grams±5 grams. Sixty-five eggs were in each treatment, and the total number of treatments was eight. Bottled oxygen (99.8%) was pressure-regulated for delivery to the treatment vessel at 32 pounds per square inch through a U.V. ozone generator (7.5 watt, 2,537 Å bulb) and U.V. chamber (7-inch diameter× 14-inch length). The ozone generated from oxygen was 0.5 grams/cubic meter of oxygen at 32 pounds per square inch. Sixty-five eggs were placed in the pressure vessel and sealed. The vacuum level was selected to be 28.5 inches of mercury with elapsed time to full vacuum being 2.5 minutes. At 28.5 inches of mercury, evacuation of the chamber was stopped and the eggs were held for five minutes. The equilibrated oxygen in the U.V. chamber at thirty.-two pounds per square inch was slowly fed into the egg vessel to restore ambient pressure. The $O_2/O_3$ continued to be fed into the chamber for about ten minutes until thirty-two pounds per square inch was achieved. The thirty-two pounds per square inch was held for five minutes. Immediately thereafter, the exhaust valve of the pressure vessel containing the eggs was opened and the oxygen and ozone were exhausted until the chamber achieved ambient pressure. The time from the exhaust of pressured oxygen/ozone to ambient pressure was approximately one minute. The eggs were removed from the chamber and the process repeated seven times until five hundred twenty eggs had been treated per test. After removal from the chamber, the time from the process until the eggs "set" in the incubator ranged from five to one hundred twenty minutes. Temperature throughout the process and preincubation hold time was 60° F.±5° F.

The results were as follows:

|  | Hatched | Unhatched | % | % Increase |
|---|---|---|---|---|
| Control Group | 435 | 85 | 83.7 |  |
| Group #1 | 458 | 62 | 88.1 | 5.3 |
| Control Group | 417 | 103 | 80.2 |  |
| Group #2 | 437 | 83 | 84.0 | 4.7 |
| Control Group | 444 | 76 | 85.4 |  |
| Group #3 | 463 | 57 | 89.0 | 4.2 |
| Control Group | 437 | 83 | 84.0 |  |
| Group #4 | 467 | 53 | 89.8 | 6.9 |
| Control Group | 433 | 87 | 83.3 |  |
| Group #5 | 456 | 64 | 87.7 | 5.3 |
| Control Group | 470 | 50 | 90.4 |  |
| Group #6 | 489 | 31 | 94.0 | 4.0 |
| Control Group | 422 | 98 | 81.2 |  |
| Group #7 | 462 | 58 | 88.8 | 9.4 |
| Control Group | 450 | 70 | 86.5 |  |

-continued

|  | Hatched | Unhatched | % | % Increase |
|---|---|---|---|---|
| Group #8 | 471 | 49 | 90.6 | 4.7 |
| Control Group | 433 | 87 | 83.3 |  |
| Group #9 | 457 | 63 | 87.9 | 5.5 |
| Control Group | 434 | 86 | 83.5 |  |
| Group #10 | 456 | 62 | 87.7 | 5.0 |

The average increase in hatch for all ten groups was 5.5%.

| Grow-Out Test | Hatched | Unhatched | % | % Increase |
|---|---|---|---|---|
| Control Group | 435 | 85 | 83.7 |  |
| Group #11 | 458 | 62 | 88.1 | 5.3 |

After hatch, both the treated and control chicks from Group No. 11 were then transported to a grow-out facility where feed consumption and body weight were monitored weekly.

Feed consumption is typically calculated based on the amount of feed necessary to increase the bird weight by one pound. This is referred to in the industry as the feed conversion ratio. Efficiencies in feeding have increased so dramatically in recent years that there is little room for improvement. However, industry estimates indicate that even small reductions in the feed conversion ratio measured to the second decimal point are significant, and can represent substantial savings to the poultry producer. Results of the feed conversion analysis are listed in the table below.

Results:

FEED CONVERSION
(Pounds of Feed:Pounds Gained)

| Group | 6 Days | 13 Days | 20 Days | 45 Days | Reduction % |
|---|---|---|---|---|---|
| Control | 0.935 | 1.232 | 1.391 | 1.986 |  |
| Treated | 0.922 | 1.161 | 1.372 | 1.975 | 0.55 |

Differences in body weight were determined by individual chick weight measurement for both control and treated chicks. The table below is an average of the body weight data collected on the treated and control chicks.

Results:

BODY WEIGHT
(Pounds)

| Group | 6 Days | 13 Days | 20 Days | 45 Days | Reduction % |
|---|---|---|---|---|---|
| Control | 0.250 | 0.591 | 1.324 | 5.133 |  |
| Treated | 0.268 | 0.667 | 1.428 | 5.267 | 2.61 |

EXAMPLE 2

Figure 2:
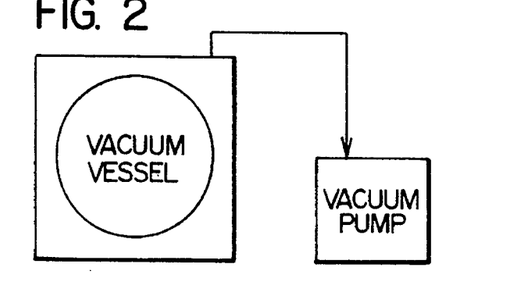
FIG. 2 is a block diagram of a second exemplary process of the present invention.
Figure 9:
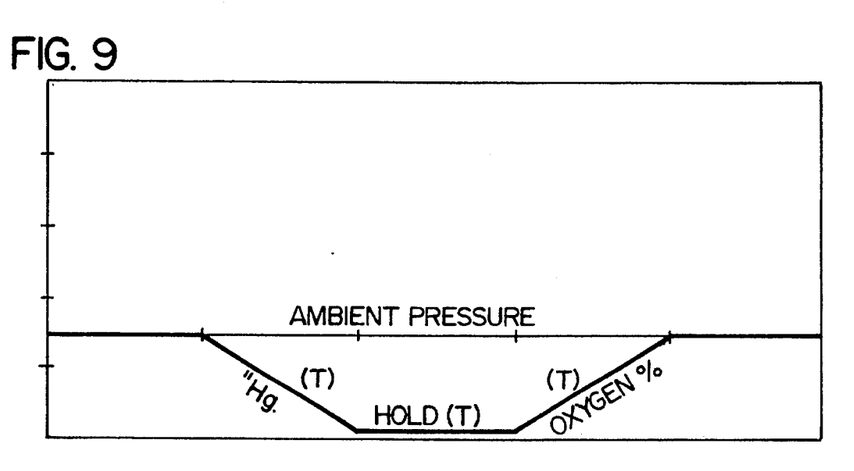
FIG. 9 is a graphical representation of the vacuum process of the present invention.

Of 1,728 fertilized eggs, 576 were held as controls and 288 were subjected to a vacuum of 29.8 inches of mercury for ten minutes, pressurized to ambient with filtered air only, and then placed in an incubator as shown in FIG. 2 and FIG. 9.

Figure 3:
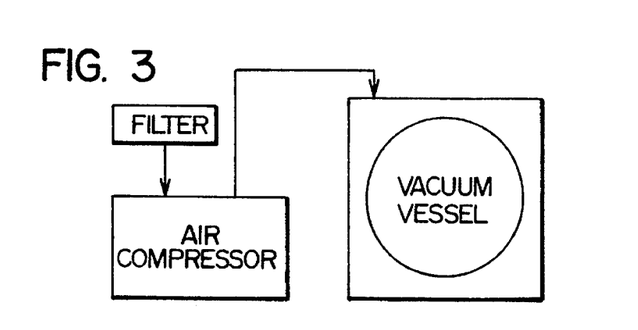
FIG. 3 is a block diagram of a third exemplary process of the present invention.
Figure 10:
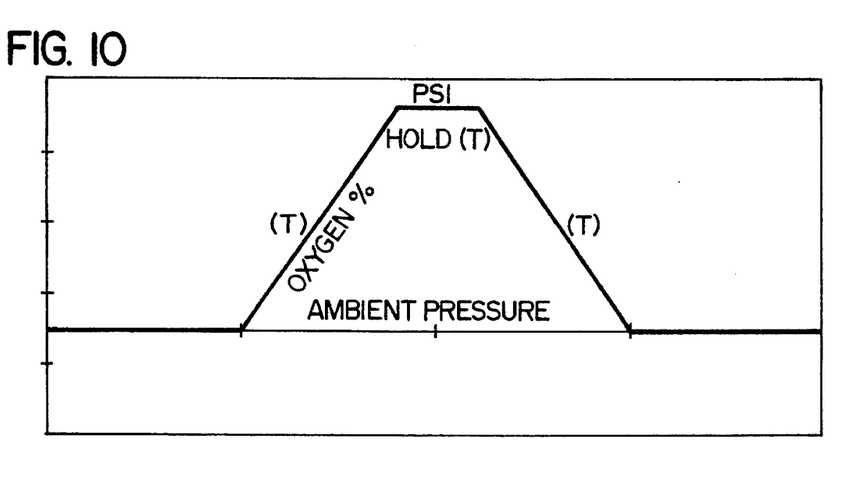
FIG. 10 is a graphical[ representation of the pressure process of the present invention.

Another 288 fertilized eggs were placed in a pressure chamber for fifteen minutes with filtered ambient air only at 28 pounds per square inch and then placed in the same incubator as shown in FIG. 3 and FIG. 10.

Another 288 fertilized eggs were subjected to both 29.8 inches of mercury vacuum for 10 minutes and pressurized with filtered ambient air only for fifteen minutes at 28 pounds per square inch as shown in FIG. 1 (but without U.V. generation of ozone) and FIG. 8.

Another 288 fertilized eggs were subjected to vacuum of 29.8 inches of mercury for ten minutes and immediately pressurized with $O_2/O_3$ for fifteen minutes at 28 pounds per square inch. A mixture of 99.6% pure oxygen was flushed across a 35 watt U.V. (2,537 Å) light until the ozone concentration measured by an ozone monitoring device was 4.5 grams per cubic meter of $O_2$. This mixture was flooded into the vacuum chamber to relieve the vacuum over a period of eight minutes and then allowed to pressurize the vessel to 28 pounds per square inch over a period of fifteen minutes as shown in FIG. 1 and FIG. 8.

All test lots and controls were placed randomly in the same 2,000-egg Jamesway incubator (Model No. 1080) at 60% relative humidity and a temperature of 99.5° F.±0.5° F.

Results:

| Group | Hatched | Unhatched | Hatch % | % Increase |
|---|---|---|---|---|
| Control | 488 | 88 | 84.7 | |
| Group #1 (Vacuum only) | 235 | 53 | 81.6 | −3.7 |
| Group #2 (Pressure only) | 238 | 50 | 82.6 | −2.5 |
| Group #3 (Pressure/Vacuum) | 231 | 57 | 80.2 | −5.3 |
| Group #4 (Vacuum/pressure/$O_3$) | 260 | 28 | 90.3 | +6.6 |

These results demonstrate the bactericidal effectiveness of pressure and vacuum and the beneficial effects of $O_2/O_3$ on fertilized egg mortality when applied prior to incubation and early prenatal phases of the egg.

EXAMPLE 3

Example 1 was repeated, except that no pressure cycle was employed, see FIG. 1 and FIG. 8, excluding the pressure cycle. The chamber was brought from vacuum to ambient, then exhausted and the eggs were removed for incubation.

Results:

| | Hatched | Unhatched | Hatch % | % Increase |
|---|---|---|---|---|
| Controls | 430 | 90 | 82.7 | |
| Group #1 | 438 | 82 | 84.2 | 1.8 |
| Controls | 420 | 100 | 80.8 | |
| Group #2 | 434 | 86 | 83.5 | 3.3 |
| Controls | 431 | 89 | 82.9 | |
| Group #3 | 454 | 66 | 87.3 | 5.3 |

The average increase over control was about 3.5%

This test shows the profound effect of $O_2/O_3$ when added to the vacuum intake. (Compare these results with the test results in which $O_2/O_3$ was not employed.)

EXAMPLE 4

Example 3 was repeated except that only ambient air was drawn into the vacuum intake with no oxygen/ozone, see FIG. 2 and FIG. 9.

Vacuum treatment alone of fertilized eggs without the benefit of oxygen, and particularly ozone, results in significant increased mortality when compared to the controls.

Results:

| | Hatched | Unhatched | Hatch % | % Increase |
|---|---|---|---|---|
| Controls | 433 | 87 | 83.3 | |
| Group #1 | 418 | 102 | 80.4 | −3.5 |
| Controls | 450 | 70 | 86.5 | |
| Group #2 | 434 | 86 | 83.5 | −3.5 |
| Controls | 454 | 66 | 87.3 | |
| Group #3 | 441 | 79 | 84.8 | −2.9 |

EXAMPLE 5

The protocol of Example 3 was followed except that only pressure (no oxygen or ozone) was employed; see FIG. 3 and FIG. 10. Air was supplied by a two horsepower, two-stroke air compressor through a carbon filter.

Pressure treatment alone of fertilized eggs without benefit of oxygen, and in particular ozone, results in a significant increased mortality when compared to the controls.

Results:

| | Hatched | Unhatched | Hatch % | % Increase |
|---|---|---|---|---|
| Controls | 431 | 89 | 82.9 | |
| Group #1 | 423 | 97 | 81.3 | −1.9 |
| Controls | 440 | 80 | 84.6 | |
| Group #2 | 428 | 92 | 82.3 | −2.7 |
| Controls | 456 | 64 | 87.7 | |
| Group #3 | 441 | 79 | 84.8 | −3.3 |

EXAMPLE 6

Figure 4:
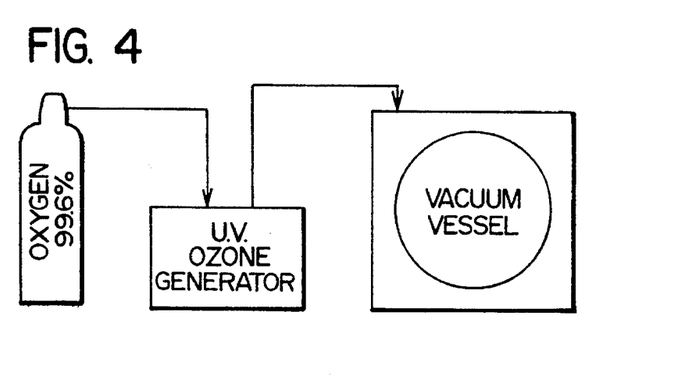
FIG. 4 is a block diagram of a fourth exemplary process of the present invention.

As shown in FIG. 4 and FIG. 10, pressure treatment alone of fertilized eggs with oxygen, and in particular ozone, results in significant increased hatch rates over the controls. The oxygen and ozone were supplied at thirty two pounds per square inch.

Results:

| | Hatched | Unhatched | Hatch % | % Increase |
|---|---|---|---|---|
| Controls | 444 | 76 | 85.4 | |
| Group #1 | 463 | 57 | 89.0 | 4.2 |
| Controls | 420 | 100 | 80.8 | |
| Group #2 | 434 | 86 | 83.5 | 3.3 |
| Controls | 423 | 97 | 81.3 | |
| Group #3 | 437 | 91 | 84.0 | 3.3 |
| Controls | 439 | 81 | 84.4 | |
| Group #4 | 456 | 64 | 87.7 | 3.9 |

EXAMPLE 7

As shown in FIG. 1 and FIG. 8 (without pressure cycle), vacuum treatment alone of fertilized eggs with oxygen, and in particular ozone, results in significant increased hatch rates over the controls. Oxygen and ozone were supplied to 28.5 inches of mercury.

Results:

| | Hatched | Unhatched | Hatch % | % Increase |
|---|---|---|---|---|
| Controls | 467 | 53 | 89.8 | |
| Group #1 | 476 | 44 | 91.5 | 1.9 |
| Controls | 439 | 81 | 84.4 | |
| Group #2 | 456 | 64 | 87.7 | 3.9 |
| Controls | 425 | 95 | 81.7 | |
| Group #3 | 440 | 80 | 84.6 | 3.5 |

Chicks from Control 2 and Group 2 were grown separately for twenty-three days. Mortality in the control group was ten birds, or a loss of 2.3%. For the test group it was seven birds, or a loss of 1.5%.

EXAMPLE 8

Test 1

Non-invasive injection of hydrogen peroxide solutions through the shell pores of fertile eggs results in significant hatch increase.

500 milliliters of an 8% solution of hydrogen peroxide was added to the reservoir of a 3 milliliter capacity peristaltic delivery pump attached to a plastic-tipped nozzle five inches long by ¼ inch in diameter with a bore of approximately one millimeter. The pump line pressure during the positive phase measured sixty-five pounds per square inch.

Results:
| Test 1 | Hatched | Unhatched | Hatch % | % Increase |
|---|---|---|---|---|
| Controls | 441 | 79 | 84.8 | |
| Group #1 | 456 | 64 | 87.7 | 3.4 |
| Controls | 427 | 93 | 82.1 | |
| Group #2 | 440 | 80 | 84.6 | 3.0 |
| Controls | 442 | 78 | 85.0 | |
| Group #3 | 455 | 65 | 87.5 | 2.9 |
| Controls | 470 | 50 | 90.4 | |
| Group #4 | 489 | 31 | 94.0 | 4.0 |

Increased hatch at the use levels of hydrogen peroxide was over 3%.

Test 2

Figure 5A:
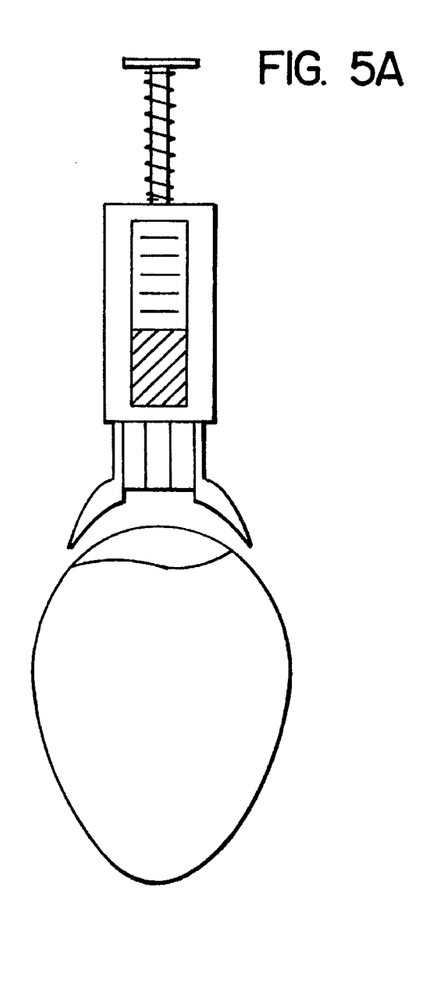
FIGS. 5A–5C are schematic representations of a non-invasive localized oxygen/ozone augmenting process and apparatus of the present invention.
Figure 5B:
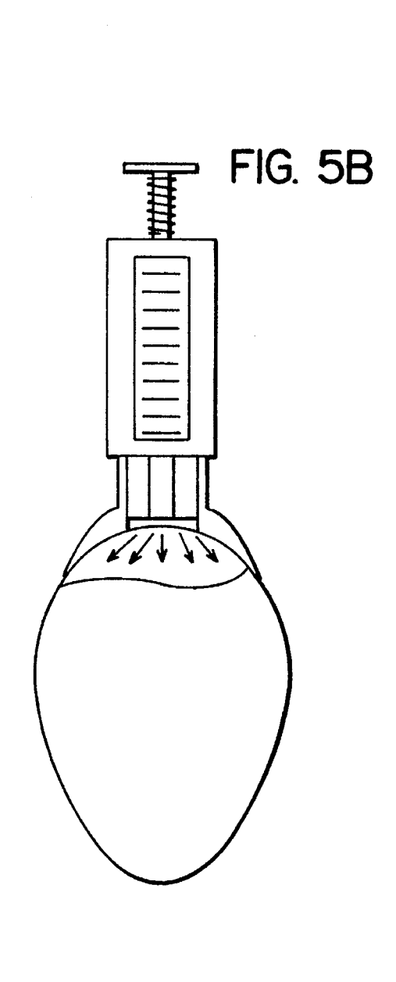
Figure 5C:
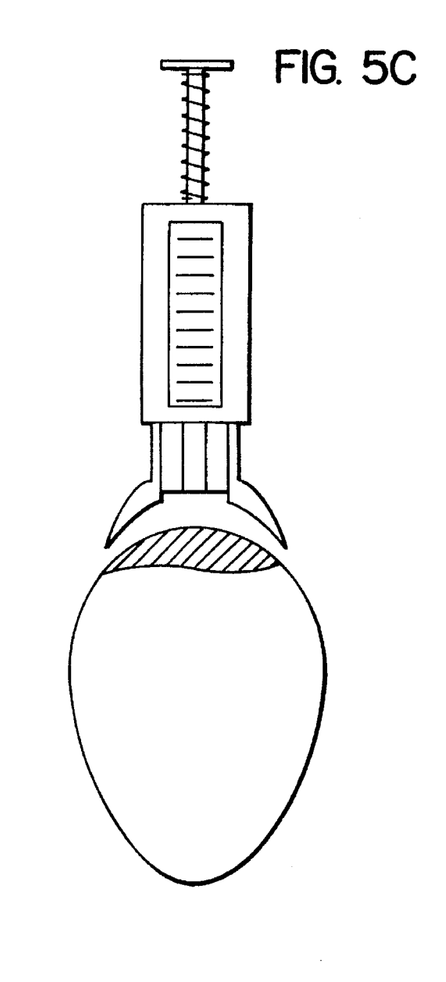

Referring to FIGS. 5A through 5C, concentrated ozone in air (>1,000 parts per million ozone to 99.6% pure oxygen) was directed onto the rounded (top) end of fertilized eggs in a high pressure burst. Delivery was by a controlled delivery, high velocity spring-loaded impact piston (2 cubic centimeters at >100 pounds per square inch).

Results:
| Test 2 | Hatched | Unhatched | Hatch % | % Increase |
|---|---|---|---|---|
| Controls | 440 | 80 | 84.6 | |
| Group #1 | 455 | 65 | 87.5 | 3.4 |
| Controls | 427 | 93 | 82.1 | |
| Group #2 | 440 | 80 | 84.6 | 3.0 |

EXAMPLE 9

Same test as Example 8, except distilled water and 2.0% solution of potassium permanganate were used in the injector.

Results:
| | Hatched | Unhatched | Hatch % | % Increase |
|---|---|---|---|---|
| Controls | 427 | 93 | 82.1 | |
| Group #1 | 437 | 83 | 84.0 | 2.3 |
| Controls | 441 | 79 | 84.8 | |
| Group #2 | 453 | 67 | 87.1 | 2.7 |
| Controls | 430 | 90 | 82.7 | |
| Group #3 | 442 | 78 | 85.0 | 2.8 |

The increased hatch at use levels of potassium permanganate was about 2.5%.

EXAMPLE 10

Figure 6:
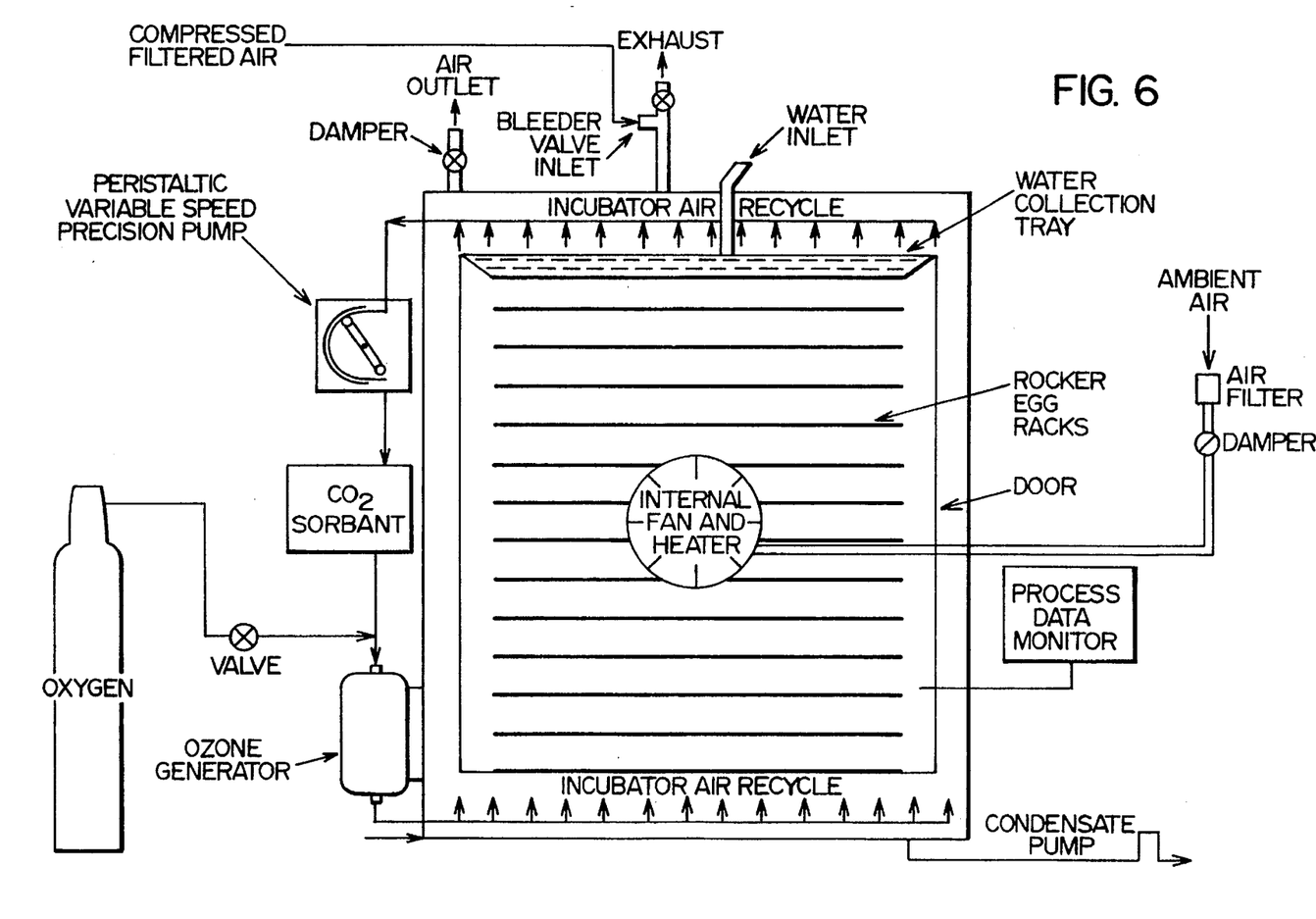
FIG. 6 is a schematic representation of a non-invasive systemic oxygen/ozone augmenting process and apparatus of the present invention.

A Jamesway model 1080 incubator was modified in accord with FIG. 6. Specifically, the incubator was reinsulated with 1.5 inch R-90 insulation sheets and made air tight by the addition of seals and silicone caulking along all open seams or leakage points. Tightly closeable dampers were fixed in the air inlet and outlet lines of the unit so that all incoming or outgoing ambient air could be sealed off by closing or opening the dampers. The condensate exit line was affixed to a positive displacement pump which automatically emptied condensate when humidity increased above 60%±2% for the first eighteen days and 70%±2% for the last three days of incubation. Oxygen, ozone, humidity, air pressure, carbon dioxide and temperature were monitored by probes. Data acquisition was recorded every ten seconds and stored in an IBM-compatible computer. Automatic controllers were operated for humidity and temperature compensation. Oxygen and ozone were monitored and physically increased or decreased by opening or closing an oxygen regulator valve and by activating or deactivating the U.V. ozone generator module (2537 Å). $CO_2$ build-ups were sorbed in an inline impingement scrubber containing 10% KOH and water to limit $CO_2$ build-up to no more than 0.5%.

The test used one thousand eggs as subjects and one thousand as controls. Both incubators were modified to the same specifications except the control incubator was fed from a two horsepower compressor through an adjustable air regulator. Air intake from the compressor was first filtered through a charcoal and fiber filter. $CO_2$ was absorbed in the same manner as in the oxygen/ozone incubator.

The control and the oxygen treatment incubators were set to 99.5° F.±0.5° F. and 60%±2% relative humidity for the first eighteen days and 70%±2% relative humidity for the last three days. Gas transport turnover per incubator was at the rate of about six liters per hour. The top-mounted air bleeder exhaust was adjusted to permit ambient air intake through the partially opened filtered air intake damper to achieve an average oxygen concentration of 39% in the oxygenated incubator with 0.21 grams of ozone per liter of oxygenated recirculated air. Carbon dioxide was controlled to a constant <0.5% above ambient levels throughout the tests. Pressure was adjusted by opening the air bleeder valve and filtered ambient air damper until ambient pressure was achieved. The units were operated immediately after loading for a period of twenty-eight hours. Immediately afterward the oxygen and U.V. ozonation unit and air compressor were deactivated. Air intake dampers for both systems were opened and air outlet dampers were left in the closed position. Air bleeder valves were left about 10% open.

The eggs hatched on the twenty-first day from commencement of incubation. Oxygen/ozone treated eggs began hatching about eight hours before controls.

Results:
| | Hatched | Unhatched | Hatch % | % Increase |
|---|---|---|---|---|
| Controls | 829 | 171 | 82.9 | |
| Group #1 | 862 | 138 | 86.2 | 4.0 |
| Controls | 841 | 159 | 84.1 | |
| Group #2 | 869 | 131 | 86.9 | 3.3 |
| Controls | 832 | 168 | 83.2 | |
| Group #3 | 858 | 142 | 85.8 | 3.1 |

EXAMPLE 11

The protocol of Example 10 was repeated, except that the oxygenated incubator air pressure was adjusted to five to six pounds per square inch.

Results:

|  | Hatched | Unhatched | Hatch % | % Increase |
|---|---|---|---|---|
| Controls | 859 | 141 | 85.9 | |
| Group #1 | 888 | 112 | 88.8 | 3.4 |
| Controls | 867 | 133 | 86.7 | |
| Group #2 | 913 | 87 | 91.3 | 5.3 |

Chicks from Group 1 and Control 1 were grown separately for three weeks.

Mortality in Group 1 group was ten birds, a loss of 1.2%. In the control group it was seventeen birds, a loss of 2%.

EXAMPLE 12

The protocol of Example 10 was repeated except that the incubators were operated normally for forty-eight hours before initiating tests.

Results:

|  | Hatched | Unhatched | Hatch % | % Increase |
|---|---|---|---|---|
| Controls | 831 | 169 | 83.1 | |
| Group #1 | 858 | 142 | 85.8 | 3.2 |
| Controls | 800 | 200 | 80.0 | |
| Group #2 | 834 | 166 | 83.4 | 4.3 |

EXAMPLE 13

The following examples illustrate the non-invasive addition of chemicals other than oxygen and ozone through the egg shell without compromising the structural integrity of the shell. One thousand fertilized eggs were held as controls and one thousand treated according to the protocol of Example 1.

A ½ inch diameter porous bandage was saturated on the adsorption pad with 0.8 milliliter distilled water and 0.3 milliliter of Omaha Vaccine Company, Marek's disease vaccine and affixed to the rounded top (point of highest porosity) of each of the one thousand eggs to be force-enriched with oxygen/ozone.

Two hundred fifty control and two hundred fifty oxygen-treated and forced-vaccinated eggs were destroyed after fourteen days and the embryos tested individually for positive and negative vaccine. The other five hundred were hatched after twenty-one days from initiation of incubation.

Results:

VACCINE PENETRATION EMBRYO RESULTS

|  | Positive | Negative |
|---|---|---|
| Test 1 | | |
| Controls | 0 | 250 |
| Treated | 247 | 3 |
| Test 2 | | |
| Controls | 0 | 250 |
| Treated | 249 | 1 |

HATCH RESULTS

|  | Hatched | Unhatched | Hatch % | % Increase |
|---|---|---|---|---|
| Test 1 | | | | |
| Controls | 634 | 116 | 84.5 | |
| Treated | 659 | 91 | 87.9 | 4.0 |
| Test 2 | | | | |
| Controls | 629 | 121 | 83.9 | |
| Treated | 661 | 89 | 88.1 | 5.0 |

EXAMPLE 14

Example 13 was repeated using Omaha Vaccine Chic-N-Pox vaccine.

Results:

VACCINE PENETRATION EMBRYO RESULTS

|  | Positive | Negative |
|---|---|---|
| Test 1 | | |
| Controls | 0 | 250 |
| Treated | 250 | 0 |
| Test 2 | | |
| Controls | 0 | 250 |
| Treated | 246 | 4 |

HATCH RESULTS

|  | Hatched | Unhatched | Hatch % | % Increase |
|---|---|---|---|---|
| Test 1 | | | | |
| Controls | 642 | 108 | 85.6 | |
| Treated | 664 | 86 | 88.5 | 3.4 |
| Test 2 | | | | |
| Controls | 634 | 116 | 84.5 | |
| Treated | 665 | 85 | 88.7 | 5.0 |

EXAMPLE 15

Marek's vaccine was introduced under the same conditions as Example 6 and in the same dosages as in Example 13.

Results:

VACCINE PENETRATION EMBRYO RESULTS

|  | Positive | Negative |
|---|---|---|
| Test 1 | | |
| Controls | 0 | 250 |
| Treated | 225 | 25 |
| Treated | 249 | 1 |

HATCH RESULTS

|  | Hatched | Unhatched | Hatch % | % Increase |
|---|---|---|---|---|
| Test 1 | | | | |
| Controls | 213 | 37 | 85.2 | |
| Treated | 220 | 30 | 88.0 | 3.2 |

The above results clearly demonstrate the feasibility of obtaining effective vaccinations through the pores of the fertile egg without sustaining losses incurred during the traditional invasive vaccinations of hatched chicks.

The advantages of vaccinating through the shell is further intensified when combined with forced enhancement of oxygen methods. Almost any form of vaccination suitable for chicks can be accomplished by methods discussed in the present invention.

EXAMPLE 16

Growth promoters, including antibiotics and micronutrients, are also effectively conveyed non-invasively through the shell without compromising the structural integrity of the shell, thus favorably influencing hatch rate, early chick survival and increased feed conversions. Gallimycin was introduced under same conditions as Example 6, using the same dosages as in Example 13.

Results:
VACCINE PENETRATION EMBRYO RESULTS

|  | Positive | Negative |
|---|---|---|
| Controls | 0 | 250 |
| Treated | 225 | 25 |

HATCH RESULTS

|  | Hatched | Unhatched | Hatch % | % Increase |
|---|---|---|---|---|
| Controls | 213 | 37 | 85.2 |  |
| Treated | 220 | 30 | 88.0 | 3.2 |

Chlortetracycline, bacitracin, virginiamycin, bambermycin and lincomycin were all tested on twenty-five eggs by the above procedure. All were found to have also penetrated the egg to the shell membrane surface.

EXAMPLE 17

Referring to FIGS. 7A through 7H, a suction cup apparatus which is engaged on the shell, preferably at the point of most pores (the egg top above the air sac), may be used to apply any or all of the foregoing forms of vacuums or pressures in order to non-invasively transfer oxygen, ozone and/or other chemicals through the shell. Two fluid lines separately communicate with the cup of the cup apparatus, as shown in FIGS. 7A through 7H.

Figure 7A:
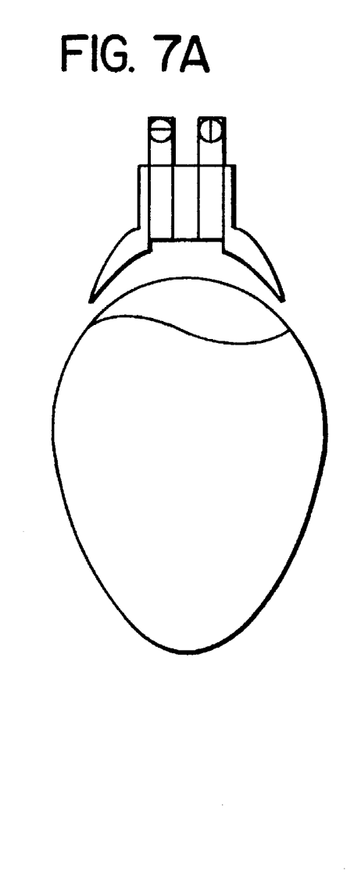
FIGS. 7A–7H are schematic representations of a second non-invasive localized oxygen/ozone augmenting process and apparatus of the present invention.
Figure 7B:
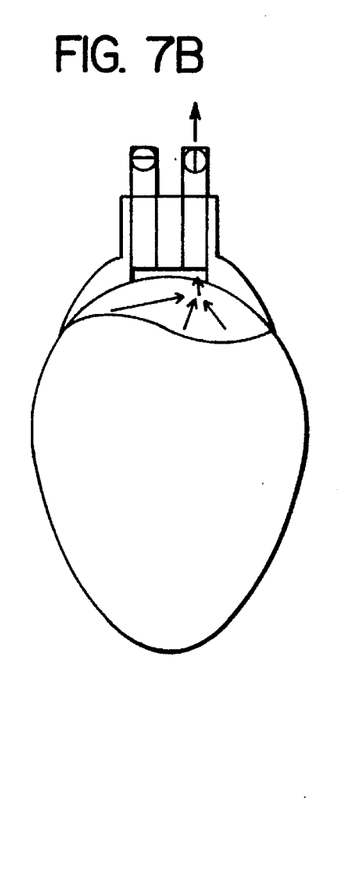
Figure 7C:
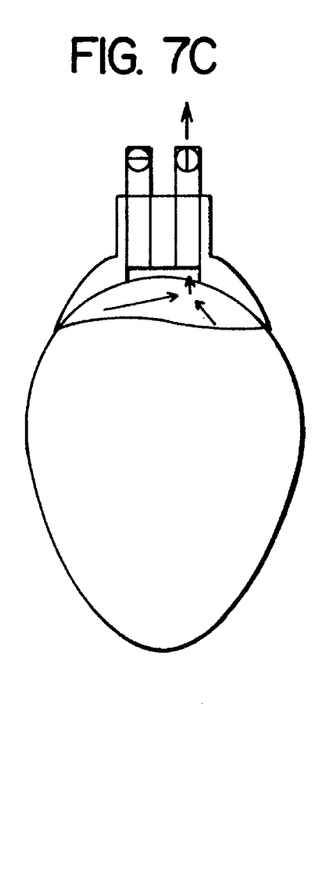
Figure 7D:
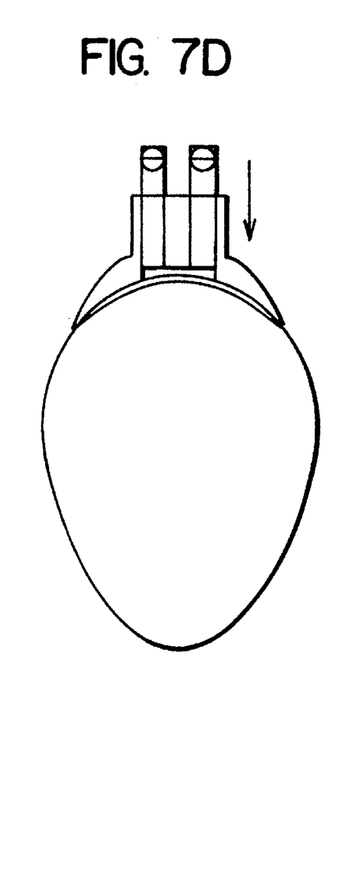
Figure 7E:
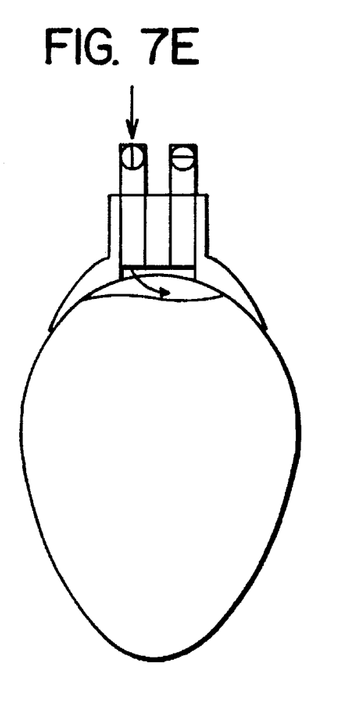
Figure 7F:
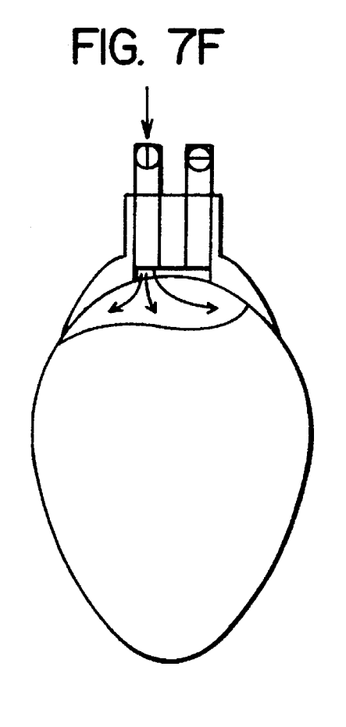
Figure 7G:
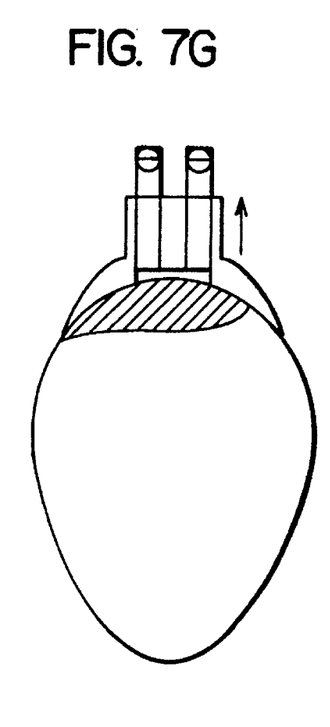
Figure 7H:
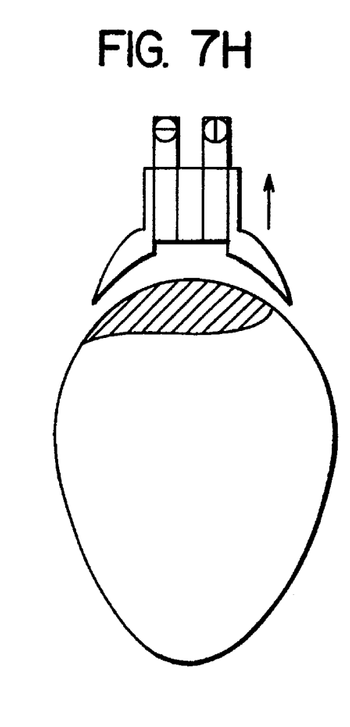

FIG. 7A shows the cup apparatus prior to engagement to the shell surface. FIG. 7B shows the apparatus immediately after engaging the surface, with negative pressure being applied. FIG. 7C shows the egg air sac being emptied by negative pressure through a line of the cup. FIG. 7D shows the emptied air sac and the cup being pressure-fitted more snugly to deliver the positive pressure fluid treatment commencing at FIG. 7E. FIG. 7F shows the air sac being filled with treating agent until full at FIG. 7G, whereupon the added pressure fit is released and the egg disengaged at FIG. 7H.

The above arrangement is similar to currently used egg transfer machines which, by suction against the egg, can be employed to lift and convey eggs from one location to another. These machines can be modified to conduct different treatments through the core of the engaging device, which in this instance is shown as a suction cup apparatus with a center plenum for enabling fluid transfers between the cup and egg. The inlet and outlet lines communicate through the center of the cup with on and off valves which may be operated independently. The cup apparatus for egg engagement is convenient, but any comparable engagement device which will not damage the egg or breach the egg shell will suffice, and also any form of inlet/outlet lines, whether one or more is used, may be used.

Using the above apparatus, the egg may be engaged by the contact device and pressure applied. If the pressure is negative, the air sac will be emptied until it conforms to the inside of the egg shell. After emptying the air sac, treating agents such as oxygen and/or ozone, antibiotics, growth promoters, hormones, micronutrients and vaccines may then be introduced under neutral or positive pressure. If positive pressure is applied, such as in a fluid stream, then the apparatus can be held against the egg to permit positive pressure to build and force treating agents through the pores. This action can be continued until the air sac has been refilled with the desired treating agent.

Treatment may be limited to negative pressure, with ambient pressure, positive pressure, or combinations thereof. For example, Examples 1, 3, 6, 7 and 8 with treating agents selected from any or all of those described in foregoing examples may be employed with the above apparatus.

An advantage to the present treatment is that the egg can be candled while being processed in order to view the condition of the air sac. This resulted in the ability to shorten the process times of Example 1 as follows: the 28.5 inches of mercury vacuum cycle was run until the air sac conformed to the inside of the egg shell, approximately twenty-five seconds, and a hold time at 28.5 inches of mercury of approximately forty seconds was used; release of the vacuum with oxygen and/or ozone (time until neutral pressure) was approximately fifteen seconds; the pressure was increased to thirty-two pounds per square inch for approximately forty-five seconds, until the air sac had returned to at least original size; and release of pressure to ambient was approximately fifteen seconds. The total time of the Example 1 protocol was reduced to approximately two hours and twenty minutes.

Results:

| Test 1 | HATCH Hatched | Unhatched | Hatch % | % Increase |
|---|---|---|---|---|
| Controls | 85 | 15 | 85.0 |  |
| Group #1 | 90 | 10 | 90.0 | 5.9 |
| Controls | 83 | 17 | 83.0 |  |
| Group #2 | 88 | 12 | 88.0 | 6.0 |
| Controls | 85 | 15 | 85.0 |  |
| Group #3 | 87 | 13 | 87.0 | 2.4 |
| Controls | 84 | 16 | 84.0 |  |
| Group #4 | 88 | 12 | 88.0 | 4.8 |

EXAMPLE 18

Fifteen eggs were each treated by the method of Example 17, whereby various chemicals were non-invasively infused through the egg shell.

Results:

| Amount With $O_2/O_3$ | Positive | Negative | Amount* Injected | Amount* Recovered |
|---|---|---|---|---|
| Probiotic mixture of *Strep. lactis* and *Strep. faecalis* | 12 | 3 | 100 | unknown |
| $CuCl_2$ | 15 | 0 | 15 | 8.00 |
| $KI_2$ | 15 | 0 | 1 | 0.65 |
| $FeSO_4$ | 15 | 0 | 100 | 70.00 |
| $ZnCl_2$ | 15 | 0 | 80 | 40.00 |
| Mo | 14 | 1 | 1 | 0.80 |
| Biotin | 15 | 0 | 1 | 0.20 |
| Choline | 10 | 5 | 1,000 | 500.00 |
| Folic acid | 14 | 1 | 5 | 0.60 |

-continued

| Results: Amount With O₂/O₃ | Positive | Negative | Amount* Injected | Amount* Recovered |
|---|---|---|---|---|
| Niacin | 12 | 3 | 30 | 12.00 |
| Pantothenic acid | 15 | 0 | 10 | 6.00 |
| Riboflavin | 11 | 4 | 5 | 2.00 |
| Thiamine | 10 | 5 | 3 | 1.00 |
| B-6 | 14 | 1 | 3 | 1.00 |
| B-12 (cobalamin) | 15 | 0 | 1 | 0.08 |

*Amounts are in milligrams

While particular embodiments of the present invention have been described in some detail herein above, changes and modifications may be made in the illustrated embodiments without departing from the spirit of the invention.

I claim:

1. A method of non-invasively infusing a fertilized avian egg with oxygen such that the structural integrity of the shell of the egg is not compromised, said method comprising the steps of:

first subjecting the external surface of the eggshell to a vacuum of from about 28.5 inches of Hg to about 29.8 inches of Hg for a time about 40 seconds to about 10 minutes; and then subjecting the external surface of the eggshell to oxygen at least at ambient pressure whereby the hatch rate of the oxygen-infused fertilized egg is greater than that of a fertilized egg not so infused with oxygen; wherein said oxygen is from a source selected from the group of consisting of pressurized oxygen and compressed air.

2. The method of claim 1 wherein all of the external surface of the eggshell is subjected to vacuum.

3. The method of claim 1 wherein only a portion of the external surface of the eggshell is subjected to vacuum.

4. A method of non-invasively infusing a fertilized avian egg with oxygen such that the structural integrity of the shell of the egg is not compromised, said method comprising the steps of:

first subjecting the external surface of the eggshell to a vacuum of from about 28.5 inches of Hg to about 29.8 inches of Hg for a time from about 40 seconds to about 10 minutes; and then subjecting the external surface of the eggshell to pressurized oxygen from a pressure source having a pressure greater than ambient pressure, said pressure being from about 5 PSI to about 32 PSI for a time from about 45 seconds to about 28 hours whereby the hatch rate of the oxygen-infused egg is greater than that of a fertilized egg not so infused with oxygen; wherein said oxygen is from a source selected from the group of consisting of pressurized oxygen and compressed air.

5. The method of claim 4 wherein all of the external surface of the eggshell is subjected to vacuum.

6. The method of claim 4 wherein only a portion of the external surface of the eggshell is subjected to vacuum.

7. A method of non-invasively infusing a fertilized egg with oxygen such that the structural integrity of the shell of the egg is not compromised, said method comprising the steps of:

first subjecting the external surface of the eggshell to a vacuum of from about 28.5 inches of Hg to about 29.8 inches of Hg for a time from about 40 seconds to about 10 minutes; and then subjecting the external surface of the eggshell to pressurized oxygen from a pressure source having a pressure greater than ambient pressure, said pressure being from about 5 PSI to about 32 PSI for a time from about 45 seconds to about 28 hours; wherein said oxygen is from a source selected from the group of consisting of pressurized oxygen and compressed air.

8. The method of claim 7 wherein all of the external surface of the eggshell is subjected to vacuum.

9. The method of claim 7 wherein only a portion of the external surface of the eggshell is subjected to vacuum.

10. A method of non-invasively infusing a fertilized egg with a mixture of oxygen and ozone such that the structural integrity of the shell of the egg is not compromised, said method comprising the steps of:

first subjecting the external surface of the eggshell to a vacuum of from about 28.5 inches of Hg to about 29.8 inches of Hg for a time from about 5 minutes to about 10 minutes; and then subjecting the external surface of the eggshell to a pressurized mixture of oxygen and ozone at a range of 0.5 to 4.5 grams per cubic meter of oxygen having a pressure from about 28 PSI to about 32 PSI for a time from about 10 minutes to about 28 hours whereby the hatch rate of the oxygen-infused fertilized egg is greater than that of a fertilized egg not so infused with oxygen.

11. The method of claim 10 wherein all of the external surface of the eggshell is subjected to vacuum.

12. The method of claim 10 wherein only a portion of the external surface of the eggshell is subjected to vacuum.

* * * * *